United States Patent [19]

Yu et al.

[11] Patent Number: 5,032,507

[45] Date of Patent: Jul. 16, 1991

[54] POTENTIATION OF ERYTHROPOIESIS

[75] Inventors: John Yu; Alice L. Yu; Joan Vaughan, all of San Diego; Jean E. F. Rivier; Wylie W. Vale, Jr., both of La Jolla, all of Calif.

[73] Assignees: The Salk Institute for Biological Studies, San Diego; The Regents of the University of California, Berkeley; Scripps Clinic and Research Foundation, La Jolla, all of Calif.

[21] Appl. No.: 120,470

[22] Filed: Nov. 13, 1987

[51] Int. Cl.$^5$ ............................ A01N 1/02; C12Q 1/02
[52] U.S. Cl. ........................................... 435/29; 435/2; 435/810; 424/93; 604/4
[58] Field of Search ................. 435/2, 29, 810; 514/2, 514/12, 814, 21; 424/9, 93; 530/300; 604/4

[56] References Cited

FOREIGN PATENT DOCUMENTS

0210461A2 4/1987 European Pat. Off. .

OTHER PUBLICATIONS

Sugino, H. et al., Biochem. Biophys. Res. Comm., vol. 153, No. 1, 1988, pp. 281-288.
Hasegawa, Y., et al., Biochim. Biophys. Res. Comm., vol. 156, No. 2, 1988, pp. 668-674.
Kitaoka, N., et al., Biochem. Biophys. Res., Comm., vol. 146, No. 3, 1987, pp. 1382-1385.
Yu, J., et al., Nature, vol. 330, 24/31 Dec. 1987, pp. 765-767.
Murata, M. et al., Proc. Natl. Acad. Sci. USA, vol. 85, pp. 2434-2438, Apr. 1988.
Broxmeyer, H., et al., Proc. Natl. Acad. Sci. USA, vol. 85, pp. 9052-9056, Dec. 1988.
Yu, J., et al., Blood, vol. 73, No. 4, Mar. 1989, pp. 952-960.
Eto, Y., vol. 142, No. 3, Boichem. Biophys. Res. Comm., pp. 1095-1103, Feb. 1987.
Alberts, B., et al., Molecular Biology of the Cell, Garland Publishing, New York, NY, 1983, pp. 925-926.
Schwall, R., et al., Endocrinology, vol. 125, No. 3, 1420-1423 (1989).

Primary Examiner—Esther L. Kepplinger
Assistant Examiner—Toni R. Scheiner
Attorney, Agent, or Firm—Fitch, Even, Tabin & Flannery

[57] ABSTRACT

A method for modulating the rate of erythropoiesis in human hematopoietic progenitor cells. FRP is found to be an efficacious potentiator of, and inhibin a suppressor of, erythropoietin-induced differentiation. FRP and inhibin are shown to be functional antagonists of each other, and thus represent an effective means for modulating erythropoiesis in a number of disease states which are directly caused by or associated with an abnormal rate of erythropoiesis.

3 Claims, No Drawings

POTENTIATION OF ERYTHROPOIESIS

This invention was made with Government support under HD-13527, HD-32826, DK-267741 and DK-37039 awarded by the National Institutes of Health (DHHS) and under NCI-5R01. The Government has certain rights in this invention.

The present invention relates generally to the field of hematology. More particularly, the invention relates to a method for augmenting or diminishing the rate of erythropoiesis in humans by administering an effective dose of FSH-releasing protein (hereinafter FRP) or inhibin, respectively.

BACKGROUND OF THE INVENTION

Blood cells are derived from progenitor cells which are derived from hematopoietic stem cells. The process whereby it is determined whether a stem cell will ultimately differentiate to form erythrocytes or leukocytes is a complex and not well understood process thought to be controlled by hormonal signals received by the cells during maturation. Although the precise scheme of hematopoiesis is not presently understood, the role of some hematopoietically-active agents is.

The process by which stem cells are induced to become mature red blood cells, erythropoiesis, is under the control of erythropoietin, a glycoprotein hormone synthesized primarily in the kidneys. Erythropoietin, which itself is regulated by the number of circulating erythrocytes, induces progenitor cells to become committed to differentiate into erythrocytes.

Several mammalian cell lines serve as models for studying erythropoiesis. These cell culture models differ as to the species from which they were derived (e.g., mouse, human, etc.) and as to their relative stage of erythrodifferentiation. Both the species of origin and the stage of maturation of a cell line are important parameters which must be considered when studying erythropoiesis. Many biologically-active molecules involved in the process of red cell differentiation have a marked effect in one species, but no activity in another. Also, proteins which clearly affect erythrodifferentiation at one stage of development may have no effect at a later or earlier stage. Thus, narrow specificities in the activity of molecules active in erythrodifferentiation are commonly seen.

The K562 cell line is a human cell line characteristic of cells at a relatively mature stage in erythrodifferentiation. It expresses such red cell markers as glycophorin A, spectrin and antigen i. K562 cells undergo differentiation and accumulate hemoglobin (one of several heme proteins, and the essential one for binding and transporting oxygen) upon induction by hemin or other chemical inducers.

A cell line that has been used to study erythrodifferentiation in mice is the mouse Friend leukemia cell line. It is a model for differentiation established with Friend virus. Several chemical inducers that work in this mouse cell line do not work with human cell lines. Furthermore, the presently known chemical inducers for these cell lines are not the physiological regulators for erythropoiesis in vivo.

Therefore, results derived from studies conducted on certain cell lines do not assure that the same biological agent will work in an in vivo system or in cells which may be at a different stage of development and/or which may be derived from a different species.

In this respect, bone marrow is a significant source of progenitor cells for the study of erythrodifferentiation. Progenitor cells cultured from bone marrow respond to many physiological hematopoietic factors found in vivo.

A preparation of placental extract was shown by Ikawa et al., Gann. 66, 583–584 (1975) to enhance δ-aminolevulinic acid synthetase and the percentage of benzidine staining cells (i.e., heme-containing cells) in a mouse Friend leukemia cell culture. Recently, using the same mouse cell line, Eto, et al., Biochem. Biophys. Res. Comm. 142, 1095–1103 (1987), reported that EDF (erythroid differentiating factor) increased the percentage of cells staining for an unidentified heme protein, and that EDF and porcine FRP had similar amino-termini.

Inhibin, a heterodimeric protein consisting of an α-subunit (18,000 daltons) and one of two B subunits ($\beta_A$ or $\beta_B$) (14,000 daltons), and FRP, a homodimer consisting of a pair of B subunits, are functionally antagonistic, hypophysiotropic hormones which were shown by Vale, et al., Nature 321, 776–779 (1986) to respectively suppress and enhance the secretion of follicle-stimulating hormone (FSH).

We have found, unexpectedly, that FRP and inhibin exert a novel and complex humoral regulatory control over erythropoiesis in humans. FRP induces hemoglobin accumulation in K562 cells, and inhibin functionally antagonizes this effect. In addition to the regulatory effect on hemoglobin accumulation, FRP and inhibin have profound augmenting (FRP) and suppressing (inhibin) activity on erythropoietin-induced proliferation and differentiation of bone marrow progenitor cells.

SUMMARY OF THE INVENTION

One method of the invention relates to increasing the number of red blood cells (RBCs) in the bloodstream and/or the hemoglobin concentration in blood. FRP potentiates the proliferation and erythrodifferentiation of erythroid progenitor cells cultured from bone marrow, and the differentiation and accumulation of hemoglobin in K562 cells. Although FRP potentiation of bone marrow cultures is dependent on the presence of erythropoietin to initiate erythrodifferentiation, FRP is a very efficacious enhancer of erythropoiesis in both cell culture systems.

K562 cells treated with picomolar concentrations of FRP accumulate hemoglobin and become terminally differentiated with limited capacity for growth. The increase in the concentration of hemoglobin in erythroid cells on a single cell basis, when compared to other inducers of erythroid differentiation, is about double (i.e., although certain compounds may induce more cells to differentiate than does FRP, cells in which erythrodifferentiation was potentiated by FRP produce about twice the amount of hemoglobin on a per cell basis).

FRP similarly causes up to a 300% increase in erythrodifferentiation in bone marrow cultures induced with erythropoietin, as compared to inducement with erythropoietin alone.

Inhibin is the functional antagonist of FRP, suppressing spontaneous erythrodifferentiation in K562 cell cultures, FRP-induced erythrodifferentiation in K562 cells, and FRP-potentiated differentiation in bone marrow cultures induced with erythropoietin. FRP and inhibin thus provide a novel humoral regulatory effect on erythrodifferentiation in much the same manner as inhibin and FRP have been shown by Vale, et al. supra, to regulate gonadotropin homeostasis.

DETAILED DESCRIPTION OF THE PREFERRED EMBODIMENT

The term "CFU-E" or "erythroid colony-forming unit" as used herein refers to a progenitor cell derived from an hematopoietic stem cell which, when induced by erythropoietin, becomes committed to proliferate and differentiate to generate a colony of about 15-60 mature erythrocytes (which can be recognized in 7 days in a human bone marrow culture).

As used herein the term "potentiate" refers to the ability of FRP to augment the rate of commitment to erythroid differentiation.

The term "erythrodifferentiation-potentiating capacity" as used herein refers to the relative difference in the number of erythropoietin-inducible CFU-Es with and without a maximally-effective amount of FRP.

One embodiment of the present invention is directed to a method for in vivo regulation of the number of progenitor blood cells that will differentiate into erythroid cells and regulating the concentration of hemoglobin in blood. The method is useful for increasing hemoglobin in treating diseases like anemia or hypoxia in which symptoms are caused by abnormal or otherwise undesirable hemoglobin or red blood cell count.

Augmenting the rate of erythropoiesis with FRP is clinically useful for treatment of congenital or acquired aplastic or hypoplastic anemia; amelioration of anemia associated with cancer, AIDS, chemotherapy, radiotherapy, bone marrow transplantation and chronic diseases; increasing red cell production in long distance runners and patients undergoing elective surgery; countering hypoxia at high altitude. Lowering the rate of erythropoiesis with inhibin is useful in the treatment of polycythemia vera and erythroleukemia. Furthermore, FRP and inhibin may control the growth and differentiation of erythroleukemia and other malignant cells.

In some clinical situations, modulating the rate of erythrodifferentiation may be useful to lower the rate of red cell production. For example, to afford a measure of protection to erythropoietic precursor cells from chemotherapeutic agents, the rate of erythropoiesis may be lowered by administration of inhibin prior to therapy, thus putting erythroid precursors in a quiescent state. Thereafter, FRP may be given to overcome the suppressing effect of inhibin and reestablish a normal rate of erythropoiesis.

FRP and inhibin may be administered, by injection, ingestion, inhalation, or other methods, such as intranasal administration. It is preferred that the method of administration be parenteral, such as by intravenous, subcutaneous or intramuscular injection or otherwise. The daily dosage of FRP or inhibin should be between about 1-50 μg of protein/kilogram of body weight, provided that the preparation is substantially pure (~98-100%) and of high specific activity. The dimers may be in the form of pharmaceutically acceptable non-toxic salts, such as acid addition salts or metal complexes, e.g., with zinc, iron, calcium, barium, magnesium, aluminum or the like. Illustrative of such acid addition salts are hydrochloride, hydrobromide, sulphate, phosphate, tannate, oxalate, fumarate, gluconate, alginate, maleate, acetate, citrate, benzoate, succinate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

It is also contemplated that in vivo erythropoiesis may be augmented in vitro by obtaining a sample of bone marrow cells, as is known in the art, potentiating erythropoietin-induced differentiation with FRP and infusing the FRP-treated cells back into the patient.

Another embodiment of the invention concerns assaying the erythropoietic capacity of an individual. In certain disease states such as anemia and hypoxia, erythropoietin levels may be elevated. It would be desirable to know the capacity of the hematopoietic system to produce still more red blood cells by potentiating erythropoiesis with FRP. An analysis of such a capacity for an increased rate of red cell generation would be useful to a physician determining a course of treatment. Furthermore, even if erythropoietin levels are normal, FRP can potentiate whatever normal rate of erythropoiesis is present.

One assay for making such a determination utilizes freshly obtained bone marrow precursor cells or precursor cells from another appropriate source which cells are seeded in culture vessels in a suitable growth medium containing methylcellulose for growth and detection of CFU-Es. Such cultured cells are induced with an effective amount of erythropoietin with or without a potentiating amount of FRP. The cultures are incubated for a suitable time at 37° C. in a humidified atmosphere (95% air; 5% $CO_2$) to allow CFU-E formation and the number of colonies are scored and compared to determine the degree of potentiation that FRP caused.

Another assay can essentially be performed in vivo by administering FRP and monitoring erythropoiesis by red cell count or hemoglobin concentration with time.

A further embodiment of the invention encompasses a diagnostic kit. In addition to erythropoietin and FRP, a kit may include means for obtaining hematopoietic precursor cells, suitable culture medium for carrying out growth of precursor cells through the stage of CFU-E formation, and tissue culture vessels suitable therefor. Because tissue culture vessels, suitable growth medium, and other supplies and instruments may be commonly available in the laboratory, a diagnostic kit could consist of FRP and erythropoietin of suitable purity for assay purposes. Generally what is required for suitable purity may be empirically determined as one skilled in the art would appreciate.

K562 cells were cultured in RPMI 1640 supplemented with 15% fetal calf serum with and without various concentration of FRP. Incubation of the cells with FRP for 3 days did not adversely effect K562 cell proliferation, as compared to control cell cultures. A clonal assay (see Rowley, et al., *Blood* 65, 862-868 (1985), in which cells were grown in RPMI 1640 culture medium containing 0.8% methylcellulose supplemented with 0, 1, 5 or 10 ng/ml FRP showed that plating efficiencies were 97% (1 ng/ml), 90% (5 ng/ml) and 92% (10 ng/ml). Thus, FRP is not cytotoxic to K562, as are some chemical inducers known in the art.

FRP induces an increase in the rate of erythroid differentiation in K562 cells. Clonal assays performed on K562 cells in the presence of FRP revealed that colonies grown in the presence of FRP were smaller (about 16 cells) than colonies formed in the absence of FRP (predominantly 32+ cells. That the FRP treated cultures, but not the control cultures, had limited capacity for further growth, and that the cultures stained benzidine-positive for hemoglobin was indicative of being erythrodifferentiated. Thus, picomolar concentrations of FRP induce K562 cells to become terminally differentiated.

K562 cells grown in RPMI 1640 with 15% fetal calf serum spontaneously differentiated at a relative low rate (i.e., approximately 6%). K562 cells grown in the same medium except supplemented with FRP show significantly higher rate of erythrodifferentiation. Culture medium made 300 picomolar with respect to FRP(10 ng/ml) induced the maximum amount of cells which stained benzidine-positive. Greater concentrations of FRP failed to induce more cells to differentiate. The half-maximal rate of induction occurred at approximately 1 ng/ml (i.e., 30 pM). Thus, the capacity to induce differentiation at such low concentration indicates that K562 cells have high affinity receptors for FRP.

The amount of hemoglobin in K562 cells treated with or without FRP or hemin was determined by cell lysis and measurement of hemoglobin by the spectrophotometric assay described in Tsiftsoglou, et al., *Cancer Res.* 39, 3849–3855 (1979), and the results are represented in Table I.

TABLE I

Hemoglobin Contents in Control and Various Induced K562 Cells

| Inducers | Hb Content/ $10^6$ cells | Benzidine Staining Cells |
|---|---|---|
| 1. None | 0.06 μg | 6% |
| 2. FRP, 10 ng/ml | 1.37 μg | 48% |
| 3. Hemin, 25 μM | 1.50 μg | 94% |

Table 1 shows that 48% of the FRP induced cells stained positive as compared to 94% of hemin induced cells. Importantly, however, FRP-treated cultures produced essentially as much hemoglobin per culture as did the hemin-treated cultures. Thus, on a single cell basis, FRP is approximately twice as effective in inducing hemoglobin production as is hemin. FRP is similarly efficacious when compared to other chemical inducers of erythrodifferentiation (data not shown). The hemoglobin isolated from lysed FRP-treated cells is shown to be mainly embryonic as assessed by immunoassays, globin chain analyses and isoelectric focusing gels.

FRP, in picomolar concentrations, also potentiates erythropoietin-induced differentiation of human bone marrow progenitor cells. Bone marrow cells grown in culture will erythrodifferentiate only if the culture medium is supplemented with erythropoietin. Erythropoietin is known to cause certain progenitor cells, that is CFU-Es, to proliferate (i.e., undergo a series of divisions) which proliferation terminates with the production of differentiated, mature red blood cells. In Table II, below, inducement of erythroid progenitor cells to differentiate was assessed by scoring hemoglobinized colonies expressing after 7 days, the well-known, unique morphology characteristic of CFU-Es.

TABLE II

Effect of FRP on Colony Formation of CFU-E from Human Bone Marrow

| | Units/ml of Erythropoietin | | | |
|---|---|---|---|---|
| | 0 | 0.2 | 0.5 | 3.0 |
| Additive: | Mean Colony Number ± S.D./$10^5$ Cells | | | |
| 1. None | 0 | 13.3 ± 2.5 (100%) | 26.3 ± 2.3 (100%) | 41.3 ± 5.1 (100%) |
| 2. FRP, 1 ng/ml | 0 | 17.7 ± 2.5 (133%) | 34.3 ± 7.3 (130%) | 78.7 ± 8.5 (191%) |
| 3. FRP, 5 ng/ml | 0 | 24.0 ± 3.6 (181%) | 39.7 ± 5.6 (151%) | 94.3 ± 7.6 (228%) |
| 4. FRP, 10 ng/ml | 0 | 39.3 ± 3.5 (296%) | 43.6 ± 6.5 (166%) | 121.6 ± 17.8 (295%) |

As shown by Table II, FRP has an enhancing effect on erythropoietin-induced differentiation in bone marrow cultures. Although 1 ng/ml of FRP might not have had a statistically significant enhancing effect, the addition of more than 5 ng/ml of FRP to cultures in the presence of erythropoietin did significantly potentiate proliferation of CFU-E colonies (p<0.01 in the t-test). As compared to the control culture which received erythropoietin alone (row 1), FRP caused approximately a 150–300% increase (rows 3 and 4).

Inhibin exerts a suppressive action which opposes induction of erythroid differentiation, especially when it is FRP-potentiated. This result is analogous to the earlier findings that inhibin and FRP exert opposite biological actions on hormone secretions by pituitary cells which effectively modulate hormone levels. Table III represents the results of an experiment in which K562 cells were cultured with or without inhibin and/or FRP for 3 days and then stained with benzidine.

TABLE III

Effect of FRP and Inhibin on Induction of K562 Cells to Differentiation

| | FRP (ng/ml) | | | |
|---|---|---|---|---|
| | 0 | 1 | 5 | 10 |
| | Benzidine Staining Cells (%) | | | |
| Inhibin, 0 ng/ml | 6 ± 1 | 23 ± 3 | 32 ± 6 | 41 ± 3 |
| Inhibin, 1 ng/ml | 1 ± 1 | 8 ± 2 | 21 ± 2 | 26 ± 5 |
| Inhibin, 5 ng/ml | 3 ± 2 | 8 ± 1 | 12 ± 3 | 16 ± 2 |
| Inhibin, 10 ng/ml | 3 ± 1 | 3 ± 2 | 9 ± 1 | 11 ± 2 |
| Inhibin, 50 ng/ml | 2 ± 1 | 4 ± 1 | 6 ± 4 | 9 ± 1 |

As shown, the addition of inhibin to cultures suppressed the FRP-induced differentiation in a dose-responsive manner. The level of half-maximal suppression was in the range of 1–5 ng/ml. The data suggest that inhibin alone did not induce differentiation, and seems to in fact suppress spontaneous differentiation.

Inhibin exhibited an analogous suppressing activity on inducement of differentiation in bone marrow cells cultures (see Table IV). Bone marrow cells were cultured using, with slight modification, the methylcellulose technique described by Ogawa, et al., *Blood*, 48, 407–417 (1976). Briefly, 1–2×$10^5$ mononuclear cells were plated in 35 mm petri dishes in 1 ml of medium, 30% fetal calf serum, 0.1 mM α-thioglycerol, 50 I.U./ml penicillin and 50 ug/ml streptomycin. FRP and/or inhibin were added in accordance with the values stated in Table IV. The dishes were incubated at 37° C. in a humidified incubator flushed with 5% $CO_2$. Incubation was carried out for 7 days and then dishes were examined on an inverted microscope for hemoglobinized colonies of CFU-E. Data on the effects of erythropoietin and FRP were subjected to two-way ANOVA statistical analysis as described at pages 321-371 in Sokol, et al., *Biometry* (W. H. Freeman and Company, 1981). The critical values for these two analyses of treatments are $F_{[3,32]}=370.4$, $F_{[3,32]}=49.5$, respectively. Similar analyses were employed to analyze the effect of inhibin by comparing the data obtained from cultures which contained erythropoietin and similar amounts of FRP with or without excess inhibin. Numbers within parentheses represent the percentage of CFU-E colony formation relative to control cultures containing similar doses of erythropoietin, but no other additives (i.e., sample #1). The symbol, n.d., represents "no determination".

TABLE IV

Effect of FRP and Inhibin on Colony Formation of CFU-E From Human Bone Marrow

| Additives: | Units/ml of Erythropoietin | | | |
|---|---|---|---|---|
| | 0 | 0.2 | 0.5 | 3.0 |
| | Mean Colony Number ± S.D./$10^5$ Cells | | | |
| 1. FRP, none | 0 | 13.3 ± 2.5 (100%) | 26.3 ± 2.3 (100%) | 41.3 ± 5.1 (100%) |
| 2. FRP, 1 ng/ml | 0 | 17.7 ± 2.5 (133%) | 34.3 ± 7.3 (130%) | 78.7 ± 8.5 (191%) |
| 3. FRP, 5 ng/ml | 0 | 24.0 ± 3.6 (181%) | 39.7 ± 5.6 (151%) | 94.3 ± 7.6 (228%) |
| 4. FRP, 10 ng/ml | 0 | 39.3 ± 3.5 (296%) | 43.6 ± 6.5 (166%) | 121.6 ± 17.8 (295%) |
| 5. FRP none + Inhibin, 10 ng/ml | 0 | 6.3 ± 2.9 (47%) | 18.3 ± 3.0 (70%) | 40.6 ± 11.0 (98%) |
| 6. FRP, 1 ng/ml + Inhibin, 5 ng/ml | 0 | 12.3 ± 4.0 (93%) | 19.0 ± 3.5 (72%) | 54.7 ± 5.5 (133%) |
| 7. FRP, 5 ng/ml + Inhibin, 10 ng/ml | 0 | 9.3 ± 2.1 (70%) | 19.3 ± 4.0 (73%) | 46.7 ± 3.2 (113%) |
| 8. FRP, 10 ng/ml + Inhibin, 25 ng/ml | 0 | n.d. | n.d. | 38.3 ± 6.4 (93%) |

As the table indicates, inhibin suppressed erythropoietin-induced CFU-E formation, even when potentiated by FRP. This inhibitory effect was strongest at lower concentration of erythropoietin; the suppressing effect of inhibin was not present at the highest concentration of erythropoietin (i.e., 3.0 units/ml). At 1 ng/ml of FRP, the addition of inhibin reduced the potentiating effect produced by FRP to about 70% of that expressed by culture which had 1 ng/ml of FRP without inhibin; and at higher concentration of FRP, the suppressive effect of inhibin became more prominent. For example, in the culture containing 10 ng/ml of FRP and excess inhibin 32% of CFU-E were produced, compared to the number produced in the culture receiving 10 ng/ml FRP without inhibin.

The results of the experiment represented in Table IV indicate that FRP and inhibin are functionally antagonistic proteins which modulate the proliferation and differentiation of erythroid progenitor cells from bone marrow. As noted above, biological activity in picomolar concentrations is indicative of the progenitor cells having receptors for FRP and inhibin. These cells may have receptors with overlapping specificities or they may have distinct receptors specific for FRP and inhibin which are then functionally antagonistic, such that the binding of inhibin interferes with initiation erythropoiesis. Alternatively, the action of inhibin might be explained if FRP, which may be culture produced, mediated the suppressive effect of inhibin. The similarities between this discovery and earlier findings respective to observations of the effects of FRP and inhibin on FSH secretion in pituitary cells, point to a mechanism in which each of these two proteins has an independent basis for activity in the absence of the other. Therefore, regardless of the precise mechanism, the bone marrow culture experiments indicate that FRP and inhibin provide humoral regulation over erythropoiesis.

FRP and inhibin have been isolated in substantially pure form from follicular fluid of various species, e.g., porcine, as well as isolating inhibin from rete testis fluid. FRP may be purified from follicular fluid using the method of Vale, et al., *Nature*, 321, 776-779 (1986), the disclosure of which is hereby incorporated by reference. Briefly, FRP is purified using ammonium sulfate precipitation, several RP-HPLC steps, cation exchange chromatography, and gel permeation chromatography. A method of purifying inhibin, employing ammonium sulfate precipitation, several reverse phase-high pressure liquid chromatography (RP-HPLC) steps, and gel permeation chromatography, is described in Rivier, J., *Biochem. Biophys. Res. Comm.*, 133, 120-127 (1985), the disclosure of which is hereby incorporated by reference.

The complete amino acid sequences of the two forms of both porcine inhibin and of human inhibin have been shown by Mason, A., et al., *Nature*, 318, 659-663 (1985) and *Biochem. Biophys. Res. Comm.*, 135, 957-964 (1986), respectively, and the disclosures of these articles are hereby incorporated by reference. Thus, three distinct genes which code for the $\alpha-$, $\beta_A-$, and $\beta_B$ subunits are responsible for the synthesis of such inhibin-related gene products.

Once a substantial portion of the sequence of a protein hormone is known, the mRNA encoding the hormone can be isolated. In this case, the mRNAs for both chains are isolated and the cDNA's are synthesized by recombinant DNA techniques. Messenger RNA (mRNA) is obtained from ovarian follicles which produce inhibin, and then cDNA is synthesized from the mRNA by reverse transcription. The cDNA is inserted into a cloning vector which is used to transform a suitable host to create a cDNA library.

More specifically, based upon the known partial amino acid residue sequence of the inhibin chains, labeled oligonucleotides are synthesized for detecting cDNA corresponding to each chain. Because of the degeneracy of the genetic code, mixed hybridization probes are prepared and used as probes. These probes are then used to select, from the library, cDNA clones that contain gene sequences encoding the chains. cDNA libraries may also be screened by immunological expression assay with an antibody raised against inhibin or one of the two inhibin chains. Immunological expression assay may also be used to confirm screening with hybridization probes.

From selected clones, cDNA is excised and inserted into appropriate vectors under the control of suitable promoter sequences, and the vectors are transformed into cell lines for expression of the recombinant inhibin chains. Although vectors containing the genes for both chains could conceivably be transformed into the same cell line, for simplicity, vectors for expression of each chain are preferably transformed separately into cell lines. The two subunit chains can then be isolated from the cellular material and/or the cell culture medium. The two chains are then subjected to oxidizing conditions which promote disulfide bonding between the chains.

It can be appreciated that using this method, various dimers of inhibin-related gene products will likely be synthesized (e.g., $\alpha\beta_A$, $\alpha\beta_B$, $\beta_A\beta_A$, $\beta_B\beta_B$, $\beta_A\beta_B$). Moreover, because it has been shown that the β-subunit is highly conserved in its amino acid sequence, the possibility exists to synthesize dimers wherein each subunit is derived from a different species, which may provide certain advantages over native dimers.

Moreover, European Patent Application S.N. 222 491 discloses a synthesis of FRP and inhibin by recombinant DNA techniques, the disclosure of which is incorporated herein by reference.

While the invention has been described with specificity, modifications apparent to those with ordinary skill in the art may be made without departing from the scope of the invention.

Various features of the invention are set forth in the following claims.

What is claimed is:

1. A method for determining the erythrodifferentiation-potentiating capacity of hematopoietic stem cells comprising:

administering to a first representative portion of said hematopoietic stem cells erythropoietin and a concentration of follicle stimulating hormone releasing protein (FRP) effective to potentiate the effect of erythropoietin in causing erythrodifferentiation, culturing said cells for a suitable length of time in a culture medium suitable for forming and detecting erythroid colony-forming units (CFU-Es); and comparing the number of CFU-Es to a control culture of said hematopoietic stem cells to determine the difference.

2. A method of increasing the population of erythrocytes in a human comprising the steps of:

a) obtaining hematopoietic progenitor cells from said human;

b) contacting said progenitor cells, under suitable culture conditions, with erythropoietin and a potentiating concentration of FSH-releasing protein (FRP) for an amount of time sufficient for at least some of said progenitor cells to develop into erythrocytes; and c) collecting said FRP-treated cells and said erythrocytes and introducing same into said human.

3. A diagnostic assay kit for testing the capacity of hematopoietic progenitor cells to undergo erythrodifferentiation comprising in one container, an amount of erythropoietin sufficient to provide doses effective to cause the differentiation of hematopoietic progenitor cells, in a separate container, a separate amount of FSH-releasing protein (FRP) sufficient to provide at least one does effective to potentiate the erythrodifferentiation action of said erythropoietin and culture vessel means for growing said hematopoietic progenitor cells in the presence of said erythropoietin and said FRP.

* * * * *

UNITED STATES PATENT AND TRADEMARK OFFICE
CERTIFICATE OF CORRECTION

PATENT NO. : 5,032,507
DATED : 07/16/91
INVENTOR(S) : YU, et al.

It is certified that error appears in the above-identified patent and that said Letters Patent is hereby corrected as shown below:

Column 1, lines 5 and 6, change "HD-13527, HD-32826, DK-267741 and DK-37039" to --Grant Nos. HD-13527, DK-26741, DK-37039 and NCI-5RO1CA40186 and Contract No. NO1-HD-3-2826--; line 6, after "Health" insert --.-- (period); line 7, delete "(DHHS) and under NCI-5RO1." Column 5, line 2, after "cells" insert --)--. Column 7, line 38, correct the spelling of "concentrations". IN THE CLAIMS: Column 10, line 24, change "does" to --dose--.

Signed and Sealed this

Fifth Day of January, 1993

Attest:

DOUGLAS B. COMER

Attesting Officer

Acting Commissioner of Patents and Trademarks